(12) United States Patent
Salzman

(10) Patent No.: US 9,981,041 B2
(45) Date of Patent: May 29, 2018

(54) OPHTHALMIC LUBRICATING SPRAY

(71) Applicant: Ira Jason Salzman, Woodbury, NY (US)

(72) Inventor: Ira Jason Salzman, Woodbury, NY (US)

( * ) Notice: Subject to any disclaimer, the term of this patent is extended or adjusted under 35 U.S.C. 154(b) by 0 days. days.

(21) Appl. No.: 15/244,617

(22) Filed: Aug. 23, 2016

(65) Prior Publication Data

US 2018/0055943 A1    Mar. 1, 2018

(51) Int. Cl.
| | |
|---|---|
| A61K 47/38 | (2006.01) |
| A61K 31/7036 | (2006.01) |
| A61M 11/00 | (2006.01) |
| A61F 9/00 | (2006.01) |
| A61K 38/13 | (2006.01) |
| A61K 31/4725 | (2006.01) |
| A61D 7/00 | (2006.01) |
| A61K 31/56 | (2006.01) |
| A61K 9/12 | (2006.01) |
| A61K 47/06 | (2006.01) |
| A61K 9/00 | (2006.01) |

(52) U.S. Cl.
CPC ............ *A61K 47/38* (2013.01); *A61D 7/00* (2013.01); *A61F 9/0017* (2013.01); *A61K 9/0048* (2013.01); *A61K 9/12* (2013.01); *A61K 31/4725* (2013.01); *A61K 31/56* (2013.01); *A61K 31/7036* (2013.01); *A61K 38/13* (2013.01); *A61K 47/06* (2013.01); *A61M 11/00* (2013.01); *A61M 2250/00* (2013.01)

(58) Field of Classification Search
None
See application file for complete search history.

(56) References Cited

U.S. PATENT DOCUMENTS

| | | | | |
|---|---|---|---|---|
| 5,294,607 | A | 3/1994 | Glonek et al. | |
| 5,588,564 | A * | 12/1996 | Hutson | A61F 9/0026 |
| | | | | 222/383.1 |

(Continued)

FOREIGN PATENT DOCUMENTS

| | | |
|---|---|---|
| CA | 2768423 A1 | 2/2011 |
| CN | 101347447 A | 7/2007 |

(Continued)

OTHER PUBLICATIONS

Pucker et al. "Over the counter (OTC) artificial tear drops for dry eye syndrome" Cochrane Database of Systematic Reviews, Feb. 23, 2016, Issue 2, pp. 1-186.*

(Continued)

*Primary Examiner* — Carlos A Azpuru
*Assistant Examiner* — Casey S Hagopian
(74) *Attorney, Agent, or Firm* — William D. Schmidt, Esq.; Sorell, Lenna & Schmidt, LLP

(57) ABSTRACT

An ophthalmic composition for administration as a spray to the eye is provided. The ophthalmic composition comprises a lubricant comprising hydroxypropyl methylcellulose (HPMC), mineral oil, and sterile water. The ophthalmic composition is also configured as a delivery vehicle for administration of ophthalmic pharmaceuticals to the eye. A method of treating keratoconjunctivitis sicca by administering the ophthalmic composition is also provided.

10 Claims, 6 Drawing Sheets
(6 of 6 Drawing Sheet(s) Filed in Color)

(56) References Cited

U.S. PATENT DOCUMENTS

| | | | |
|---|---|---|---|
| 5,643,870 A * | 7/1997 | Boelsterli | C07K 7/645 |
| | | | 514/20.5 |
| 5,989,535 A | 11/1999 | Nayak | |
| 6,610,322 B1 | 8/2003 | Keller | |
| 7,524,511 B1 | 4/2009 | Kleyne | |
| 8,071,073 B2 | 12/2011 | Dang et al. | |
| 8,569,273 B2 | 10/2013 | Abelson et al. | |
| 8,802,075 B2 | 8/2014 | Cooper et al. | |
| 9,095,585 B2 | 8/2015 | Vickery et al. | |
| 9,198,898 B2 | 12/2015 | Zhang et al. | |
| 2004/0164099 A1 | 8/2004 | Diestelhorst et al. | |
| 2005/0063996 A1 * | 3/2005 | Peyman | A61K 9/0048 |
| | | | 424/400 |
| 2006/0204474 A1 | 9/2006 | Coroneo | |
| 2006/0281739 A1 * | 12/2006 | Gadek | A61K 31/198 |
| | | | 514/227.5 |
| 2006/0287336 A1 * | 12/2006 | Prakash | A61K 31/496 |
| | | | 514/254.09 |
| 2010/0022465 A1 * | 1/2010 | Brubaker | A61K 9/0048 |
| | | | 514/29 |
| 2011/0105450 A1 | 5/2011 | Chapin et al. | |
| 2012/0003296 A1 | 1/2012 | Shantha | |
| 2014/0336618 A1 | 11/2014 | Wilkerson et al. | |

FOREIGN PATENT DOCUMENTS

| | | |
|---|---|---|
| WO | 1996000050 A1 | 6/1995 |
| WO | 2011064558 A2 | 11/2010 |

OTHER PUBLICATIONS

Pucker et al. "Over the counter (OTC) artificial tear drops for dry eye syndrome" Cochrane Database of Systematic Reviews, Feb. 23, 2016, Issue 2, pp. 1-186. (Year: 2016).*

* cited by examiner

OPHTHALMIC LUBRICATING SPRAY

BACKGROUND

Dry eye (e.g., keratoconjunctivitis sicca), can be diagnosed pathologically during ophthalmic exams as superficial punctate keratopathy (SPK) of the ocular surface epithelium. It is a common and symptomatic condition which is especially prevalent in post-menopausal women. Dry eye is defined as an abnormal state in the amount and quality of tears, and in many cases, results in insufficient tears in any one of the lipid layer, the aqueous layer and the mucin layer, thereby causing keratoconjunctivitis disorder. This condition can induce various ocular surface problems of varying degrees such as foreign body sensations, burning sensations, and damage of visual acuity in severe cases due to the damage of the conjunctiva and cornea. This includes recurrent corneal ulceration with resultant corneal scarring.

Disorders such as reduced shedding of tears, tear deficiency, dry eye syndrome, Sjogren's syndrome, keratoconjunctivitis sicca, Stevens-Johnson syndrome, ocular pemphigus, marginal blepharitis, failure of eyelid closure, sensory nerve injury, exposure keratopathy, corneal ulcers, corneal scarring, etc. are included in the category of dry eye.

One of the most common treatments of dry eye is to use an ocular instillation of artificial tears at the time when dry eye symptoms occur to temporarily supplement and stabilize the tear film. These artificial tears, which contain viscoelastic materials such as methyl cellulose, chondroitin sulfate, and hyaluronic acid, are commonly applied to the eyes as a substitute for lipid, aqueous and mucin. However, since the artificial tears are physically and physiologically different from mucin, the therapeutic effect is limited.

Another common method to treat dry eye is to use a cyclosporine A composition which is normally used as a therapeutic agent for increasing tear secretion through stabilizing the epithelial cells and increasing goblet cells in the dry eyes. Because cyclosporin A inhibits the function of helper T cells through inhibiting the formation of interleukin-2 (one of the major inflammatory cytokines), which results in reducing lymphocytic infiltration of the lacrimal gland, thereby increasing tear production, the cyclosporin A is used as an agent for treating dry eye diseases.

However, while these treatments may provide results for dry eye, they also, depending on their viscosity, can cause blurring of vision when the viscosity of the composition is high. For example, higher viscosity products are used for more severe forms of dry eye but because these products can cause blurry conditions, they are not an ideal treatment. On the other hand, compositions with a lower viscosity are not viscous enough and are less effective when used as a lubricant.

Further, while these treatments provide temporary relief and/or increase tear secretion to the eye, these treatments are often difficult to administer. Eye treatment solutions are normally self-administered by using either an eye cup or a dropper. The rim of the eye cup is configured to tightly engage against the soft tissue surrounding the eye. Because of the eye cup rim's mating anatomical design, the rim forms a positive seal when placed over the eye and gently presses against the infra-orbital tissue. A liquid such as an eye wash solution is then placed in the eye cup and the cup is held against the infra-orbital tissue of the eye. The head is tilted back to allow the solution to immerse the eye. The head may also be moved from side to side to allow the solution to be fully distributed over the cornea and the peripheral tissues of the eye.

Another popular device for self-administering a fluid to the eye is an eye dropper. The eye drop solution is delivered directly into the eye from either a dropper or a dropper type bottle. The person is usually lying down or has the head leaning back during administration. When using the dropper method of administration, one hand of the user pulls the lower lid away from the eye to expose the conjunctiva so that one or more drops of the solution can be introduced.

While most people can manage either the eye cup immersion or the eye drop method for the self-administration of a fluid to the eye, there is a segment of the population which find these devices and methods awkward or difficult to perform because of various visual and/or physical limitations. For example, individuals having partial or impaired vision, neuromuscular problems, muscular and/or skeletal disease, tremor due to Parkinson's disease and those lacking hand/wrist coordination would fall into this group. Likewise, elderly patients, the largest group of eye drop users, often have hand-eye coordination problems, tremors or arthritis, affecting the hands and/or the cervical spine, making eye drop administration difficult if not impossible. Many users report that they have trouble keeping track of their regimens and often repeat doses or miss them entirely, suffering potential consequences in either event. Further, pediatric patients and animals often fight such application which typically results in under dosing due to the patient's attempts to prevent the eye drops from being administered, or overdosing, as a result of the administrator's attempt to ensure that sufficient dosage is being applied.

Accordingly, in view of the foregoing limitations and problems discussed above, there is a need for an ophthalmic composition for administration as a spray to the eye which has an improved viscosity, can be used to apply existing treatments, is easy to use and is acceptable to a wide range of users, including those with physical and visual limitations who are unable to self-apply eye products.

SUMMARY

An ophthalmic composition for administration as a spray to the eye is provided. The ophthalmic composition comprises a lubricant comprising hydroxypropyl methylcellulose (HPMC), mineral oil, and sterile water.

In one embodiment, an ophthalmic composition for administration as a spray to the eye is provided. The ophthalmic composition comprises a therapeutic agent; and a liquid delivery vehicle comprising hydroxypropyl methylcellulose (HPMC), mineral oil, and sterile water.

In one embodiment, a method of treating an ophthalmic condition in a patient suffering therefrom is provided. The method comprises administering an effective amount of the ophthalmic composition in a spray comprising a lubricant comprising hydroxypropyl methylcellulose (HPMC), mineral oil, and sterile water to an eye of the patient.

The above and other objects, features and advantages of the present application will become apparent from the following description read in conjunction with the accompanying drawings, in which like reference numerals designate the same elements. The present application is considered to include all functional combinations of the above described features and is not limited to the particular structural embodiments shown in the figures as examples. The scope and spirit of the present application are considered to include modifications as may be made by those skilled in the art having the benefit of the present disclosure which substitute, for elements presented in the claims, devices or structures upon which the claim language reads or which are equivalent thereto, and which produce substantially the same results associated with those corresponding examples identified in this disclosure for purposes of the operation of this application. Furthermore, operations in accordance with methods of the description and claims are not intended to be required in any particular order unless necessitated by prerequisites included in the operations. Additionally, the scope and spirit of the present application is intended to be defined by the scope of the claim language itself and equivalents thereto without incorporation of structural or functional limitations discussed in the specification which are not referred to in the claim language itself. Accordingly, the detailed description is intended as illustrative in nature and not limiting the scope and spirit of the present application.

BRIEF DESCRIPTION OF THE DRAWINGS

The patent or application file contains at least one drawing executed in color. Copies of this patent or patent application publication with color drawing(s) will be provided by the Office upon request and payment of the necessary fee. As the color drawings are being filed electronically via EFS-WEB, only one set of the drawing is submitted.

Figure 1:
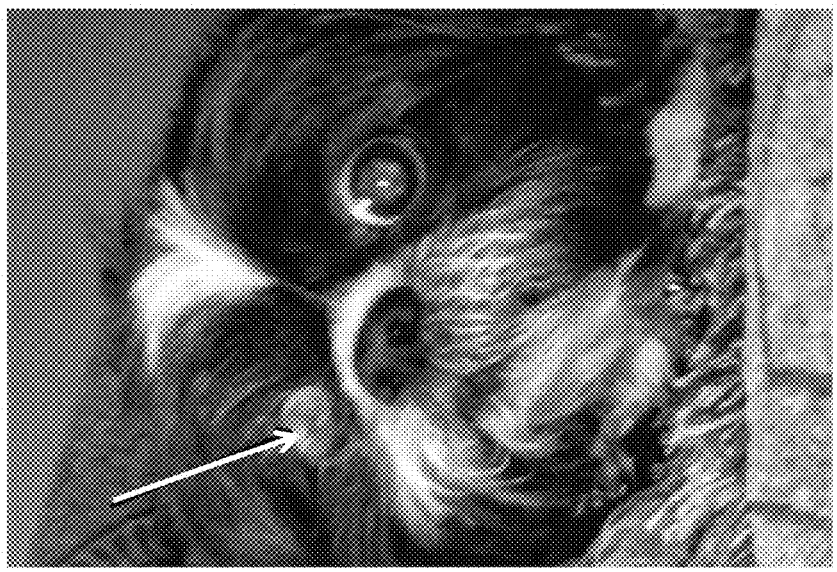
FIG. 1 is a picture of a dog suffering from dry eye with recurrent corneal ulcer and resultant corneal scarring before administration of the ophthalmic composition that is being delivered as a spray.
Figure 2:
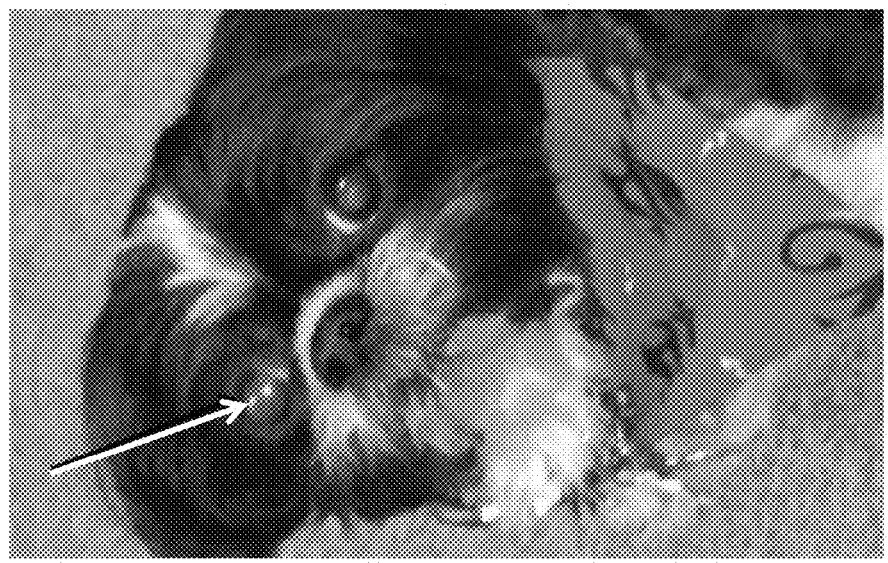
FIG. 2 is a picture of the dog in FIG. 1 after three weeks of administration of the ophthalmic composition that is being delivered as a spray.

It is to be understood that the figures are not drawn or photographed to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

The term "spray bottle", as used herein, refers to a bottle that can squirt, spray or mist fluids. A spray bottle includes, but is not limited to an aerosol or a non-aerosol bottle.

The term "aerosol", as used herein, refers to a material which is dispensed from its container as a mist, spray, or foam by a propellant under pressure, or an "aerosol product" means a product characterized by a pressurized spray system that dispenses product ingredients in aerosol form by means of a propellant (i.e., a liquefied or compressed gas that is used in whole or in part, such as a co-solvent, to expel a liquid or any other material from the same self-pressurized container or from a separate container) or mechanically induced force. In referencing the propellant, aerosol means any non-refillable receptacle containing a gas compressed, liquefied or dissolved under pressure, the sole purpose of which is to expel a nonpoisonous liquid, paste, or powder and fitted with a self-closing release device allowing the contents to be ejected by the gas.

The term "non-aerosol", as used herein, refers to pump sprays. Non-aerosol sprays are normally in a bottle with an atomizer attachment (such as a pump-sprayer). The pump sprayer uses springs, valves and tubes to mix the liquid with a small amount of air and emits the liquid as small droplets propelled in short bursts.

The term "spray", as used herein, refers to a jet of liquid in fine drops, coarser than a vapor. A spray can be produced by forcing the liquid from an opening of an atomizer, mixing it with air. In some embodiments, the term "spray" can refer herein to a cloud of droplets from about 200-500 microns, characterized by a Freefall time (existence time per minute) of about 0.05 seconds, and a terminal velocity of 2000 mm/sec. In some embodiments, the visual appearance of such a spray is droplets. In some embodiments, the term "spray" can refer to droplets from 10 to 500 microns in size.

The term "atomizer", as used herein, refers to a device used to reduce liquid compositions into fine particles in the form of a spray or aerosol.

The term "spray plume", as used herein, includes a mist generated by a device such as an aerosol or non-aerosol spray bottle. The plume can deliver a varying or specific amount of the ophthalmic composition to the eye of a person depending on the sophistication of the bottle. The plume can be manipulated into various lengths, various disbursing angles, degrees of intensity, duration and velocities depending on the sophistication of the bottle.

The term "mist" can be interchangeable with the term "spray" or "spray plume" and refers to a cloud of very small droplets provided with a Brownian motion, i.e., a cloud which is not under facilitated flow within a confined volume by any external mechanism, such as a fan or an injector. Moreover, it is directed tangentially towards a confined volume adjacent to the eye, in a manner that droplets do not collide and thus decrease their mass and subsequently impinge the eye.

An "eye dropper", as used herein, refers to a pipet comprising a small tube with a vacuum bulb at one end for drawing liquid in and releasing it a drop at a time.

"Viscosity", as used herein, refers to a liquid's resistance to flow and is ratio of the magnitude of an applied shear stress to the velocity gradient that it produces. When the intermolecular forces of attraction are strong within a liquid, there is a higher viscosity, and when the intermolecular forces of attraction are weak within a liquid, there is a lower viscosity.

"Viscosity enhancing agent", refers to agents that are used to enhance and/or increase viscosity upon dispensing the agent to the eye. In some embodiments, the agent can provide enhanced penetration of the ophthalmic composition into the eye relative to a similar liquid composition having a lower viscosity. Some viscosity enhancing agents include, but are not limited to mannitol, trehalose, hydroxypropyl cellulose, hydroxypropyl methylcellulose, hydroxyethyl methylcellulose, carboxymethylcellulose and salts thereof, Carbopol, poly-(hydroxyethyl-methacrylate), poly-(methoxyethylmethacrylate), poly(methoxyethoxyethylmethacrylate), polymethyl-methacrylate (PMMA), methylmethacrylate (MMA), gelatin, polyvinyl alcohols, propylene glycol, mPEG, and polyethylene glycol (PEG).

The term "drug" or a "therapeutic agent", as used herein, includes, but is not limited to demulcents; antimycotics, antivirals and other anti-infectives; steroids, NSAIDs, selective cyclooxygenase-2 inhibitors and other anti-inflammatory agents; acetylcholine blocking agents; adrenergic agonists, beta-adrenergic blocking agents and other antiglaucoma agents; antihypertensives; antihistamines; anticataract agents; and topical and regional anesthetics. Illustrative specific drugs include acebutolol, aceclidine, acetylsalicylic acid (aspirin), $N^4$ acetylsulfisoxazole, alclofenac, alprenolol, amfenac, amiloride, aminocaproic acid, ρ-aminoclonidine, aminozolamide, anisindione, apafant, atenolol, bacitracin, benoxaprofen, benoxinate, benzofenac, bepafant, betamethasone, betaxolol, bethanechol, bimatroprost, brimonidine, bromfenac, bromhexine, bucloxic acid, bupivacaine, butibufen, carbachol, carprofen, celecoxib, cephalexin, chloramphenicol, chlordiazepoxide, chlorprocaine, chlorpropamide, chlortetracycline, ciclopro- fen, cinmetacin, ciprofloxacin, clidanac, clindamycin, clo- nidine, clonixin, clopirac, cocaine, cromolyn, cyclopento- late, cyproheptadine, demecarium, dexamethasone, dibucaine, diclofenac, diflusinal, dipivefrin, dorzolamide, enoxacin, epinephrine, erythromycin, eserine, estradiol, ethacrynic acid, etidocaine, etodolac, fenbufen, fenclofenac, fenclorac, fenoprofen, fentiazac, flufenamic acid, flufenisal, flunoxaprofen, fluorocinolone, fluorometholone, flurbiprofen and esters thereof, fluticasone propionate, furaprofen, furobufen, furofenac, furosemide, gancyclovir, gentamicin, gramicidin, hexylcaine, homatropine, hydrocortisone, ibufenac, ibuprofen and esters thereof, idoxuridine, indomethacin, indoprofen, interferons, isobutylmethylxanthine, isofluorophate, isoproterenol, isoxepac, ketoprofen, ketorolac, labetolol, lactorolac, latanoprost, levo-bunolol, lidocaine, lonazolac, loteprednol, meclofenamate, medrysone, mefenamic acid, mepivacaine, metaproterenol, methanamine, methylprednisolone, metiazinic, metoprolol, metronidazole, minopafant, miroprofen, MK-663, modipafant, nabumetome, nadolol, namoxyrate, naphazoline, naproxen and esters thereof, neomycin, nepafenac, nitroglycerin, norepinephrine, norfloxacin, nupafant, olfloxacin, olopatadine, oxaprozin, oxepinac, oxyphenbutazone, oxyprenolol, oxytetracycline, parecoxib, penicillins, perfloxacin, phenacetin, phenazopyridine, pheniramine, phenylbutazone, phenylephrine, phenylpropanolamine, phospholine, pilocarpine, pindolol, pirazolac, piroxicam, pirprofen, polymyxin, polymyxin B, prednisolone, prilocaine, probenecid, procaine, proparacaine, protizinic acid, rimexolone, rofecoxib, salbutamol, scopolamine, sotalol, sulfacetamide, sulfanilic acid, sulindac, suprofen, tenoxicam, terbutaline, tetracaine, tetracycline, theophyllamine, timolol, tobramycin, tolmetin, travaprost, triamcinolone, trimethoprim, trospectomycin, valdecoxib, vancomycin, vidarabine, vitamin A, warfarin, zomepirac and pharmaceutically acceptable salts thereof.

The drug or therapeutic agent can be added to the ophthalmic composition at a particular percentage measured in w/w, w/v or v/v. In some embodiments, the drug or the therapeutic agent comprises about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% w/w, w/v or v/v of the ophthalmic composition.

The term "steroids" or "steroid", as used herein, includes an organic compound with four rings arranged in a specific configuration. Ophthalmic steroids are compounds specifically designed to be applied in the eyes and can include anecortive acetate, tetrahydrocortisol; 4,9(11)-pregnadien-17α,21-diol-3,20-dione, and its -21-acetate salt; 11-epicortisol; 17α-hydroxyprogesterone; tetrahydrocortexolone; cortisona; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its -21-acetate, -21-disodium phosphate, and -21-hemisuccinate forms; triamcinolone benetonide; triamcinolone hexacetonide; fluocinolone and fluocinolone acetate; dexamethasone and its 21-acetate, -21-(3,3-dimethylbutyrate), -21-phosphate disodium salt, -21-diethylaminoacetate, -21-isonicotinate, -21-dipropionate, and -21-palmitate forms; betamethasone and its -21-acetate, -21-adamantoate, -17-benzoate, -17,21-dipropionate, -17-valerate, and -21-phosphate disodium salts; beclomethasone; beclomethasone dipropionate; diflorasone;

diflorasone diacetate; mometasone furoate; acetazolamide; loteprednol; difluprednate; fluorometholone, rimexolone, medrysone, fluticasone, budesonide, and cyclosporine. The term steroid also includes anti-neovascularization steroids as 21-nor-5β-pregnan-3α,17α,20-triol-3-acetate; 21-nor-5α-pregnan-3α,17α,20-triol-3-phosphate; 21-nor-5β-pregn-17 (20)en-3α,16-diol; 21-nor-5β-pregnan-3α,17β,20-triol; 20-acetamide-21-nor-5α-pregnan-3α,17α-diol-3-acetate; 313 acetamido-5β-pregnan-11β,17α,21-triol-20-one-21-acetate; 21-nor-5α-pregnan-3α,17β,20-triol; 21α-methyl-5β-pregnan-3α,11β,17α,21-tetrol-20-1-one-21-methyl ether; 20-azido-21-nor-5β-pregnan-3α,17α-diol; 20(carbethoxymethyl)thio-21-nor-5β-pregnan-3α,17α-diol; 20-(4-fluorophenyl)thio-21-nor-5β-pregnan-3α,17α-diol; 16α-(2-hydroxyethyl)-17β-methyl-5β-androstan-3α,17α-diol; 20-cyano-21-nor-5β-pregnan-3α,17α-diol; 17α-methyl-5β-androstan-3α,17α-diol; 21-nor-5β-pregn-17(20)en-3α-ol; 21- or -5β-pregn-17(20)en-3α-ol-3-acetate; 21-nor-5-pregn-17(20)-en-3α-ol-16-acetic acid 3-acetate; 3β-azido-5-pregnan-11β,17α,21-triol-20-one-21-acetate; and 5-pregnan-11β,17α,21-triol-20-one; 4-androsten-3-one-17β-carboxylic acid; 17α-ethynyl-5(10)-estren-17β-ol-3-one; and 17α-ethynyl-1,3,5(10)-estratrien-3,17-diol.

The term "non-steroidal anti-inflammatory agents" (NSAIDs), as used herein, refers to agents such as naproxen; diclofenac; celecoxib; sulindac; diflunisal; piroxicam; indomethacin; etodolac; meloxicam; ibuprofen; ketoprofen; r-flurbiprofen; mefenamic; nabumetone; tolmetin, and sodium salts of each of the foregoing; ketorolac bromethamine; ketorolac tromethamine; choline magnesium trisalicylate; rofecoxib; valdecoxib; lumiracoxib; etoricoxib; aspirin; salicylic acid and its sodium salt; salicylate esters of α,β,γ-tocopherols and tocotrienols (and all their d, l, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; and phenylbutazone.

The term "antimicrobial", as used herein, includes chloramphenicol, neomycin sulfate, bacitracin, gentamycin, sulfacetamide and polymixin B sulfate, antifungal agents such as amphotericin, and antiviral agents, such as acyclovir among others, may be preserved with NPX.

The term "preservative", as used herein, includes imidazolidinyl urea, methylparaben, propyl paraben, phenoxyethanol, disodium EDTA, thimerosal, chlorobutanol, sorbic acid and mixtures thereof. Other preservatives include, but are not limited to Nepal ethyl paraben, benzalkonium chloride (BAK), disodium ethylenediamine tetra-acetate, polyquaternium-1 or alkyltrimethylammonium bromide, sodium perborate, polyquad, sodium chlorite, purite, or polexitonium.

The term "antibiotics", as used herein, includes gram-negative effective antibiotics can be used such as from aminoglycosides, cephalosporins, diaminopyridines, fluroquinolones, sulfonamides and tetracyclines. Among particular antibiotics of these and other classes, each of the following may illustratively be useful as a gram-negative effective antibiotic: amikacin, azithromycin, cefixime, cefoperazone, cefotaxime, ceftazidime, ceftizoxime, ceftriaxone, chloramphenicol, ciprofloxacin, clindamycin, colistin, domeclocycline, doxycycline, erythromycin, gentamicin, mafenide, methacycline, minocycline, neomycin, norfloxacin, ofloxacin, oxytetracycline, polymyxin B, pyrimethamine, silver sulfadiazine, sulfacetamide, sulfisoxazole, tetracycline, tobramycin and trimethoprim. Gram-negative effective antibiotics are fluroquinolones such as ciprofloxacin, norfloxacin and ofloxacin.

The term "antiviral", as used herein, includes iota carrageenan, VIRA-A ophthalmic ointment, (vidarabine). Opthalmic quinalones include, for example, CHIBROXIN (norfloxacin ophthalmic solution); CILOXAN ophthalmic solution, (Ciprofloxacin HCL); and Ocuflox ophthalmic solution (ofloxacin). Opthalmic sulfonamides include, for example, BLEPHAMIDE ophthalmic ointment (sulfacetamide sodium and prednisolone acetate); and BLEPH-AMIDE ophthalmic suspension (sulfacetamide sodium and prednisolone acetate).

The term "antifungal", as used herein, refers to natamycin, amorolfine, amphotericin B, anidulafungin, butoconazole, butenafine, caspofungin, ciclopirox olamine, clotrimazole, econazole, fluconazole, flucytosine, griseofulvin, haloprogin, itraconazole, ketoconazole, micafungin, miconazole (including miconazole nitrate), naftifine, nikkomycin Z, nystatin (topical and liposomal), oxiconazole, posaconazole, pimaricin, ravuconazole, sulconazole, terbinafine, terconazole, tioconazole, tolnaftate, undecylenate, voriconazole, or any other antifungal or a salt thereof The term "mast cell stabilizers", as used herein, refers to an agent that inhibits the degranulation of sensitized and/or nonsensitized mast cells. A mast cell stabilizer thus inhibits the release of inflammatory mediators, such as histamine, SRS-A, and chymase from mast cells. Mast cell stabilizers include, but are not limited to olopatadine, derivatives of olopatadine, alcaftidine, derivatives of alcaftadine, spleen tyrosine kinase inhibitors, and dihydropyridines.

Cytokine inhibitors, as used herein, inhibit the synthesis of pro-inflammatory cytokines in nonimmune resident ocular surface cells by interfering with specific effectors of signaling cascades in these cells. Effectors of cytokine synthesis targeted for inhibition in the treatment of dry eye include mitogen-activated kinases (MAP kinase, p38 kinase), c-jun N-terminal kinase (JNK) and 1-kappa kinase (IKK). Also, inhibitors of enzymes which convert precursors of the pro-inflammatory cytokines IL-1β (ICE, IL-1 converting enzyme) and TNFα (TACE, TNF-alpha converting enzyme) to the active species or inhibit the translation of cytokine mRNA provide dry eye therapy. Cytokines promote further synthesis of pro-inflammatory cytokines through activation of Janus family tyrosine kinase (JAK) and signal transducers and activators of transcription (STAT) and, therefore, inhibitors of JAKs and STATs provide treatment of dry eye. Inhibitors of activator protein-1 (AP-1) suppress cytokine synthesis in ocular surface cells and provide dry eye therapy. Additionally, ligands of retinoid X receptors (RXR) are known to suppress cytokine synthesis in epithelial cells and are suitable for use in the present invention. Inhibitors of MAP kinases (p38) include (5-(2-amino-4-pyrimidinyl)-4-(4-fluorophenyl)-1-(4-piperidinyl) imidazole) ["SB-220025"]. Inhibitors of JNK include anthra[1,9-cd]pyrazol-6(2H)-one ["SP-600125"]. Inhibitors of ICE include pralnacasan (HMR3480/VX-740). TNF mRNA translation inhibitors include (D)Arginyl-(D)Norleucyl-(D)Norleucyl-(D)Arginyl-(D)Norleucyl-(D)Norleucyl-(D)Norleucyl-Glycine-(D)Tyrosine-amide, acetate salt ["RDP58"]. NFkB inhibitors include 2-chloro-N-[3,5-di(trifluoromethyl)phenyl]-4-(trifluoromethyl)pyrimidine-5-carboxamide ["SP-100030"], and triflusal. AP-1 inhibitors include SP-100030. RXR agonists include bexarotene. In some embodiments, the cytokine inhibitor is lifitegrast.

An ophthalmically acceptable "pH adjusting agent" and/or "buffering agents", as described herein, includes acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an ophthalmically acceptable range.

An "ophthalmically acceptable salt", as described herein, can be included into the composition in an amount required to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions; sodium chloride, potassium chloride, sodium thiosulfate, sodium bisulfite and ammonium sulfate.

"Ophthalmically acceptable acids", as described herein, include an acid having at least two dissociable hydrogen groups and can be included in the composition as interactive agents to retard release of the drug/therapeutic agent. Acids useful as interactive agents include boric, lactic, orthophosphoric, citric, oxalic, succinic, tartaric and formic glycerophosphoric acids.

"Solubilizers", as described herein, may be added to the composition as needed and may be chosen for properties providing solubility of the specific therapeutic agent in question. Solubilizers that may be used include, but are not limited to polyoxyethylene glycol ethers, polyethylene glycol higher fatty acid esters, and polyoxyethylene fatty acid esters.

The term "surfactant", refers to a compound that lowers the surface tension between two liquids or between a liquid and a solid. Surfactants may act as detergents, wetting agents, emulsifiers, foaming agents, and dispersants. The composition, as described herein may further comprise an ophthalmologically acceptable surfactant to assist in dissolving the drug/therapeutic agent. The ophthalmic composition may also contain a thickener such as hydroxymethylcellulose, hydroxyethylcellulose, hydroxypropylmethylcellulose, methylcellulose, polyvinylpyrrolidone, or the like, to improve the retention of the composition in the conjunctival sac.

The term "solution", as used herein, refers to a mixture containing at least one solvent and at least one compound that is at least partially dissolved in the solvent.

The term "solvent," as used herein, means a substance, typically a liquid, that is capable of completely or partially dissolving another substance, typically a solid.

The term "suspension", as used herein, refers to a heterogeneous mixture of a fluid and solid particles.

Ophthalmic Composition as a Lubricant

In one embodiment, an ophthalmic composition as a spray is provided that is administered to treat a patient suffering from an eye condition. In some embodiments, the eye condition can include, but is not limited to, dry eye syndrome (e.g., keratoconjunctivitis sicca), meibomitis, conjunctivitis, iritis, age-related macular degeneration, glaucoma, a corneal laceration, exposure keratopathy, corneal ulcer, corneal scar and/or a traumatic corneal abrasion. In some embodiments, the patient includes, but is not limited to an animal, such as a human, dog, cat, horse, hamster, pig, cow, bird, bunny, chicken, goat, and/or a sheep. In some embodiments, the patient is an elderly human, a child or a person suffering from an illness.

In some embodiments, the ophthalmic composition comprises hydroxypropyl methylcellulose (HPMC or hypromellose), mineral oil, and sterile water. In some embodiments, the ophthalmic composition consists of HPMC, mineral oil, and sterile water. In some embodiments, the composition consists of HPMC 0.25%. In some embodiments, the ophthalmic composition is a lubricant for the eye.

In some embodiments, the ophthalmic composition comprises about 0.1% w/w to about 5% w/w of the HPMC, about 1% w/w to about 33% w/w of the mineral oil, and about 62% w/w to about 97% w/w of the sterile water. In some embodiments, the composition comprises about 0.2% w/w of the HPMC, about 20% w/w of the mineral oil, and about 79.8% w/w of the sterile water.

In some embodiments, the composition is administered via a spray that is dispensed from an aerosol bottle. In some embodiments, the composition is administered via a spray that is dispensed from a non-aerosol bottle. In some embodiments, before administration to the eye, the bottle is vigorously shaken for a period of time to form an emulsion. In some embodiments, the spray facilitates enhanced or better adherence of the composition to the cornea of the eye.

In some embodiments, the spray dispenses about 0.15 ml of the ophthalmic composition to the eye of a patient in a plume or a mist. In some embodiments, the spray dispenses about 0.05 ml to about 50 ml of the composition to the eye in a plume or a mist. In some embodiments, the spray dispenses from about 0.05, 0.06, 0.70, 0.08, 0.09, 0.10, 0.11, 0.12, 0.13, 0.14, 0.15, 0.16, 0.17, 0.18, 0.19, 0.20, 0.25, 0.30, 0.35, 0.40, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, or 40 ml of the composition to the eye in a plume or a mist.

In some embodiments, the spray dispenses about 50,000 to about 20,000,000 mcg of the composition to the eye in a plume or a mist. In some embodiments, the spray dispenses from about 50,000 to about 200,000 mcg, from about 50,000 to about 100,000 mcg, from about 50,000 to about 75,000 mcg of the composition to the eye in a plume or a mist.

In some embodiments, the composition comprises about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, 1.0, 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, 1.20, 1.21, 1.22, 1.23, 1.24, 1.25, 1.26, 1.27, 1.28, 1.29, 1.30, 1.31, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.71, 1.72, 1.73, 1.74, 1.75, 1.76, 1.77, 1.78, 1.79, 1.80, 1.81, 1.82, 1.83, 1.84, 1.85, 1.86, 1.87, 1.88, 1.89, 1.90, 1.91, 1.92, 1.93, 1.94, 1.95, 1.96, 1.97, 1.98, 1.99, 2.0, 2.01, 2.02, 2.03, 2.04, 2.05, 2.06, 2.07, 2.08, 2.09, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29, 2.30, 2.31, 2.32, 2.33, 2.34, 2.35, 2.36, 2.37, 2.38, 2.39, 2.40, 2.41, 2.42, 2.43, 2.44, 2.45, 2.46, 2.47, 2.48, 2.49, 2.50, 2.51, 2.52, 2.53, 2.54, 2.55, 2.56, 2.57, 2.58, 2.59, 2.60, 2.61, 2.62, 2.63, 2.64, 2.65, 2.66, 2.67, 2.68, 2.69, 2.70, 2.71, 2.72, 2.73, 2.74, 2.75, 2.76, 2.77, 2.78, 2.79, 2.80, 2.81, 2.82, 2.83, 2.84, 2.85, 2.86, 2.87, 2.88, 2.89, 2.90, 2.91, 2.92, 2.93, 2.94, 2.95, 2.96, 2.97, 2.98, 2.99, 3.0, 3.01, 3.02, 3.03, 3.04, 3.05, 3.06, 3.07, 3.08, 3.09, 3.10, 3.11, 3.12, 3.13, 3.14, 3.15, 3.16, 3.17, 3.18, 3.19, 3.20, 3.21, 3.22, 3.23, 3.24, 3.25, 3.26, 3.27, 3.28, 3.29, 3.30, 3.31, 3.32, 3.33, 3.34, 3.35, 3.36, 3.37, 3.38, 3.39, 3.40, 3.41, 3.42, 3.43, 3.44, 3.45, 3.46, 3.47, 3.48, 3.49, 3.50, 3.51, 3.52, 3.53, 3.54, 3.55, 3.56, 3.57, 3.58, 3.59, 3.60, 3.61, 3.62, 3.63, 3.64, 3.65, 3.66, 3.67, 3.68, 3.69, 3.70, 3.71, 3.72, 3.73, 3.74, 3.75, 3.76, 3.77, 3.78, 3.79, 3.80, 3.81, 3.82, 3.83, 3.84, 3.85, 3.86, 3.87, 3.88, 3.89, 3.90, 3.91, 3.92, 3.93, 3.94, 3.95, 3.96, 3.97, 3.98, 3.99, 4.0, 4.01, 4.02, 4.03, 4.04, 4.05, 4.06, 4.07, 4.08, 4.09, 4.10, 4.11, 4.12, 4.13, 4.14, 4.15, 4.16, 4.17, 4.18, 4.19, 4.20, 4.21, 4.22, 4.23, 4.24, 4.25, 4.26, 4.27, 4.28, 4.29, 4.30, 4.31, 4.32, 4.33, 4.34, 4.35, 4.36, 4.37, 4.38, 4.39, 4.40, 4.41, 4.42, 4.43, 4.44, 4.45, 4.46, 4.47, 4.48, 4.49, 4.50, 4.51, 4.52, 4.53, 4.54, 4.55, 4.56, 4.57, 4.58, 4.59, 4.60, 4.61, 4.62, 4.63, 4.64, 4.65, 4.66, 4.67, 4.68, 4.69, 4.70, 4.71, 4.72, 4.73, 4.74, 4.75, 4.76, 4.77, 4.78, 4.79, 4.80, 4.81, 4.82, 4.83, 4.84, 4.85, 4.86, 4.87, 4.88, 4.89, 4.90, 4.91, 4.92, 4.93, 4.94, 4.95, 4.96, 4.97, 4.98, 4.99, to about 5.0% of HPMC in w/w, w/v or v/v in the ophthalmic composition.

In some embodiments, the composition comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, to about 60% of the mineral oil in w/w, w/v or v/v. In some embodiments, the composition comprises about 5 to about 20%, about 10 to about 15% or about 15 to about 20% mineral oil in w/w, w/v or v/v.

In some embodiments, the composition comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 to about 90 of the sterile water in w/w, w/v or v/v.

In some embodiments, the composition has a viscosity of about of about 15 to about 100 centipoises (cP). In some embodiments, the composition has a viscosity of about of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100 cp. In some embodiments, the composition comprises a high viscosity and can be used for night-time application for patients suffering from severely dry corneas. In some embodiments, the composition comprises a low viscosity composition which causes less visual blur than a high viscosity composition and can be used during the day.

In some embodiments, the HPMC has a viscosity of about 2,600-5,600 cP before being added to a solution or a suspension. In some embodiments, the HMPC has a viscosity of about 28,000-54,000, 30,000-52,000, 32,000-50,000, 34,000-48,000, 36,000-46,000, 38,000-44,000, or about 40,000-42,000 cp. In some embodiments, the HPMC has a viscosity of about 2,600, 2,700, 2,800, 2,900, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, 50,000, 51,000, 52,000, 53,000, 54,000, 55,000, or 56,000 cp.

In some embodiments, the mineral oil is heavy, intermediate or light mineral oil. Heavy mineral oil has a higher, thereby thicker viscosity than both intermediate and light mineral oil. Light mineral oil has a lower, thereby thinner viscosity than both intermediate and heavy mineral oil. In some embodiments, the mineral oil has a viscosity of about 5 to about 40 cp. In some embodiments, the mineral oil has a viscosity of about 5 to about 10, about 10 to about 15, about 15 to about 20, about 20 to about 25, about 25 to about 30, about 30 to about 35, or about 35 to about 40 cp. In some embodiments, the mineral oil has a viscosity of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, to about 40 cp.

In some embodiments, a viscosity enhancing agent may be added to the composition. In some embodiments, the viscosity enhancing agent is used to enhance and/or increase viscosity upon dispensing the agent to the eye. In some embodiments, the viscosity enhancing agent can provide enhanced penetration of the ophthalmic composition into the eye relative to a similar liquid composition having a lower viscosity. In some embodiments, the viscosity enhancing agent includes, but is not limited to mannitol, trehalose, hydroxypropyl cellulose, hydroxypropyl methylcellulose, hydroxyethyl methylcellulose, carboxymethylcellulose and salts thereof, Carbopol, poly-(hydroxyethyl-methacrylate), poly-(methoxyethylmethacrylate), poly(methoxyethoxyethylmethacrylate), polymethyl-methacrylate (PMMA), methylmethacrylate (MMA), gelatin, polyvinyl alcohols, propylene glycol, mPEG, and polyethylene glycol (PEG).

In some embodiments, the viscosity enhancing agent may be added to the composition in an amount of about 0.10, 0.20, 0.30, 0.40, 0.50, 0.60, 0.70, 0.80, 0.9, 1, 2, 3, 4, 5, 6, 7, 8, 9, to about 10% w/w, w/v, or v/v.

The HPMC is a cellulose polymer, in particular, propylene glycol ether of methylcellulose. In some embodiments, the HPMC facilitates a particular viscosity for the composition. HPMC is available in a variety of grades under several trade names. The various grades differ in methoxy and hydroxypropyl content, as well as in terms of molecular weight and viscosity (of 2% solution in water at 20° C.). In some embodiments, the cellulose ether that can be used in the composition may be selected from any available grade of HPMC. Suitable material is sold by the 'The Dow Chemical Company' ("Dow") under the trademark METHOCEL. In some embodiments, the HPMC grade which may be selected to be used in the composition includes, but is not limited to: METHOCEL E, (USP grade 2910/HYPROMELLOSE 2910) including (a) METHOCEL E3 (Premium LV) having 28-30 weight percent methoxyl content, 7-12 weight percent hydroxypropyl content and viscosity of a 2% aqueous solution of 2.4-3.6 cps (b) METHOCEL E5 (Premium LV) having 28-30 weight percent methoxyl content, 7-12 weight percent hydroxypropyl content and viscosity of a 2% aqueous solution of 4.0-6.0 cps. (c) METHOCEL E6 (Premium LV) having 28-30 weight percent methoxyl content, 7-12 weight percent hydroxypropyl content and viscosity of a 2% aqueous solution of 5.0-7.0 cps (d) METHOCEL E15 (Premium LV) having 28-30 weight percent methoxyl content, 7-12 weight percent hydroxypropyl content and viscosity of a 2% aqueous solution of 12.0-18.0 cps (e) METHOCEL E50 (Premium LV) having 28-30 weight percent methoxyl content, 7-12 weight percent hydroxypropyl content and viscosity of a 2% aqueous solution of 40.0-60.0 cps (f) METHOCEL E4M (Premium) having 28-30 weight percent methoxyl content, 7-12 weight percent hydroxypropyl content and viscosity of a 2% aqueous solution of 3000.0-5600.0 cps (g) METHOCEL E1OM (Premium CR) having 28-30 weight percent methoxyl content, 7-12 weight percent hydroxypropyl content and viscosity of a 2% aqueous solution of 7500.0-14000.0 cps, METHOCEL F, (USP grade 2906/HYPROMELLOSE 2906) including (a) METHOCEL F50 (Premium) having 27-30 weight percent methoxyl content and 4-7.5 weight percent hydroxypropyl content, (b) METHOCEL F4M (Premium LV). METHOCEL K, (USP grade 2208/HYPROMELLOSE 2208) including (a) METHOCEL K3 (Premium LV) having 19-24 weight percent methoxyl content, 4-12 weight percent hydroxypropyl content and viscosity of a 2% aqueous solution of 2.4-3.6 cps (b) METHOCEL KlOO (Premium LV) having 19-24 weight percent methoxyl content, 4-12 weight percent hydroxypropyl content and viscosity of a 2% aqueous solution of 80.0-120.0 cps (c) METHOCEL K4M (Premium) having 19-24 weight percent methoxyl content, 4-12 weight percent hydroxypropyl content and viscosity of a 2% aqueous solution of 3000.0-5600.0 cps (d) METHOCEL K15M (Premium) having 19-24 weight percent methoxyl content, 4-12 weight percent hydroxypropyl content and viscosity of a 2% aqueous solution of 11,250.0-21,000.0 cps (e) METHOCEL KlOOM (Premium) having 19-24 weight percent methoxyl content, 4-12 weight percent hydroxypropyl content and viscosity of a 2% aqueous solution of 80,000.0-120,000.0 cps, METHOCEL A15 (Premium LV); METHOCEL A4C (Premium); METHOCEL A15C (Premium); METHOCEL A4M (Premium), and HPMC USP Grade 1828 having 16.5-20 weight percent methoxyl content, 23-32 weight percent hydroxypropyl content. In some embodiments, the HPMC is Goniovisc™ Hypromellose 2.5% ophthalmic (HUB Pharmaceuticals, LLC. Rancho Cucamonga, Calif. 91730).

In some embodiments, the HPMC has a molecular weight of from about 10,000 g/mol to about 110,000 g/mol. In some embodiments, the HPMC has a molecular weight from about 20,000 g/mol to about 100,000 g/mol, from about 30,000 g/mol to about 90,000 g/mol, from about 40,000 g/mol to about 80,000 g/mol, from about 50,000 g/mol to about 70,000 g/mol, or from about 60,000 g/mol to about 65,000 g/mol. In some embodiments, the HPMC has a molecular weight of about 20,000, 30,000, 40,000, 50,000, 60,000, 70,000, 80,000, 90,000, 100,000, or 110,000 g/mol.

In some embodiments, the HPMC has a particle size ranging from about 10 to about 10,000 nanometers (nm). In some embodiments, the HPMC has a particle size ranging from about 100 to about 8,000 nm, from about 500 to about 6,000 nm, from about 1,000 to about 4,000 nm, or from about 2,000 to about 3,000 nm.

In some embodiments, the HPMC has a particle size of 10, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950, 5000, 5050, 5100, 5150, 5200, 5250, 5300, 5350, 5400, 5450, 5500, 5550, 5600, 5650, 5700, 5750, 5800, 5850, 5900, 5950, 6000, 6050, 6100, 6150, 6200, 6250, 6300, 6350, 6400, 6450, 6500, 6550, 6600, 6650, 6700, 6750, 6800, 6850, 6900, 6950, 7000, 7050, 7100, 7150, 7200, 7250, 7300, 7350, 7400, 7450, 7500, 7550, 7600, 7650, 7700, 7750, 7800, 7850, 7900, 7950, 8000, 8050, 8100, 8150, 8200, 8250, 8300, 8350, 8400, 8450, 8500, 8550, 8600, 8650, 8700, 8750, 8800, 8850, 8900, 8950, 9000, 9050, 9100, 9150, 9200, 9250, 9300, 9350, 9400, 9450, 9500, 9550, 9600, 9650, 9700, 9750, 9800, 9850, 9900, 9950, or 2000 nm.

In some embodiments, the composition may include additional pharmaceutically acceptable excipients. Pharmaceutically acceptable excipients include, but are not limited to osmotic/tonicity-adjusting agents, preservatives, one or more pharmaceutically acceptable buffering agents and pH-adjusting agents, and solubilizing agents.

In some embodiments, the composition is isotonic with respect to the ophthalmic fluids present in the human eye. In some embodiments, the composition has an osmolality of about 240-400 mOsm/kg. In some embodiments, the composition has an osmolality of about 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or 400 mOsm/kg.

In some embodiments, the osmolality of the composition is adjusted by the addition of an osmotic/tonicity adjusting agent. In some embodiments, the osmotic agents may be used in the composition to make it isotonic with respect to the ophthalmic fluids present in the human eye and include, but are not limited to mannitol, glycerol, sorbitol, propylene glycol, dextrose, sucrose, and the like, and mixtures thereof. In some embodiments, an ophthalmically acceptable salt is an osmotic agent and is added to the composition to bring osmolality of the composition into an ophthalmically acceptable range. In some embodiments, the salts include but are not limited to those having sodium, potassium or ammonium cations and chloride, citrate, ascorbate, borate, phosphate, bicarbonate, sulfate, thiosulfate or bisulfite anions; sodium chloride, calcium chloride potassium chloride, sodium thiosulfate, sodium bisulfite, sodium bromide, and/or ammonium sulfate.

In some embodiments, the osmotic agent is present in the composition in an amount from about 1.0% to about 8.0% by weight of the composition, from about 4.0% to about 6.0% by weight of the composition, or from about 4 to about 5.0% by weight of the composition. In some embodiments, the osmotic agent is present in the composition in an amount from about 1, 2, 3, 4, 5, 6, 7, or 8% of the composition.

In some embodiments, the composition is preservative free. In some embodiments, the composition further comprises a preservative and a buffering agent.

In some embodiments, the ophthalmic composition comprises preservatives. In some embodiments, antimicrobial effective amounts of a preservative may be determined by performing preservative efficacy tests or antimicrobial effectiveness tests. In some embodiments, the preservative comprises about 0.01 to about 10% w/w, w/v, or v/v of the composition. In some embodiments, the preservative comprises about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 or 10% w/w, w/v or v/v of the composition.

In some embodiments, the preservative includes, but is not limited to quaternary ammonium compounds such as benzalkonium chloride (BKC) and benzethonium chloride; organic mercurials such as phenylmercuric acetate, phenylmercuric nitrate and thimerosal; Parabens such as methyl and propyl paraben; ethyl paraoxybenzoate or butyl paraoxybenzoate; acids and their pharmaceutically acceptable salts such as sorbic acid, potassium sorbate, boric acid, borax, salicylic acid; substituted alcohols and phenols such as chlorobutanol, benzyl alcohol; phenyl ethanol; amides such as acetamide, and combinations thereof. In some embodiments, the composition is self-preserving and includes a combination of zinc salts and boric acid in the presence of tromethamine. In some embodiments, the preservative includes imidazolidinyl urea, phenoxyethanol, disodium EDTA, Nepal ethyl paraben, disodium ethylenediamine tetra-acetate, polyquaternium-1 or alkyltrimethylammonium bromide, sodium perborate, polyquad, sodium chlorite, purite, or polexitonium.

In some embodiments, the composition has a pH in the range of about 5 to about 9. In some embodiments, the composition has a pH of about 6.5 to about 7.5, or about 6.9 to about 7.4. In some embodiments, the composition has a pH of about 5, 5.5, 6, 6.5, 7, 7.5, 8, 8.5 to about 9.

In some embodiments, a pH adjusting agent and/or a buffering agent is added to the composition to achieve and maintain a selected pH. In some embodiments, the pH adjusting agent and/or a buffering agent includes, but is not limited to acetic acid or salts thereof, boric acid or salts thereof, phosphoric acid or salts thereof; citric acid or salts thereof, tartaric acid or salts thereof, sodium hydroxide, potassium hydroxide, sodium carbonate, sodium hydrogencarbonate, trometamol, and mixtures thereof. In some embodiments, the pH adjusting agent is hydrochloric acid, and/or sodium hydroxide. In some embodiments, the pH adjusting agent and/or buffering agent comprises about 0.1, 0.2, 0.3, 0.4, 0.5, 0.6, 0.7, 0.8, 0.9, 1, 2, 3, 4, 5, 6, 7, 8, 9, to about 10% w/w, w/v or v/v of the composition.

In some embodiments, the composition comprises an isotonic agent such as, for example, sodium chloride, potassium chloride, boric acid, and/or borax. In some embodiments, the isotonic agent comprises from about 0.05 to about 1% w/w, w/v or v/v of the composition. In some embodiments, the isotonic agent comprises from about 0.05, 0.10, 0.15, 0.20, 0.25, 0.30, 0.35, 0.40, 0.45, 0.55, 0.60, 0.65, 0.70, 0.75, 0.80, 0.85, 0.90, 0.95, to about 1.0% w/w, w/v or v/v of the composition. In some embodiments, when sodium chloride is selected, sodium chloride is used in an amount of from about 0.75 to about 0.95%. In some embodiments, when sodium chloride, boric acid, and/or borax are selected, they may be used in an amount from about 0.05 to about 1.0%, respectively.

Ophthalmic Composition as a Delivery Vehicle

In some embodiments, the ophthalmic composition is a delivery vehicle which facilitates administration of a therapeutic agent or multiple therapeutic agents to the eye of a patient.

In some embodiments, the composition comprises a therapeutic agent; and a liquid delivery vehicle comprising hydroxypropyl methylcellulose (HPMC), mineral oil, and sterile water. In some embodiments, the liquid delivery vehicle as described herein, may contain all of or some of the features described above with regard to the composition as a lubricant.

In some embodiments, the composition comprises one part therapeutic agent to two parts liquid delivery vehicle. In some embodiments, the composition comprises one part therapeutic agent to one part delivery vehicle. In some embodiments, the composition comprises one part therapeutic agent to three parts deliver vehicle, one part therapeutic agent to four parts delivery vehicle, or one part therapeutic agent to five parts delivery vehicle.

In some embodiments, the therapeutic agent comprises a steroid, an antimicrobial, a cytokine inhibitor, an antihistamine, NSAIDS, leukotriene inhibitors or a combination thereof. In some embodiments, the composition comprises about 20% to about 33% w/w, w/v or v/v of the therapeutic agent. In some embodiments, the composition comprises about 20, 21, 22, 23, 24, 25, 26, 27, 28, 29, 30, 31, 32 to about 33% w/w, w/v or v/v of the therapeutic agent.

In some embodiments, the composition comprises from about 0.1 to about 99% w/w, w/v or v/v of the therapeutic agent. In some embodiments, the composition comprises from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% w/w, w/v or v/v of the therapeutic agent.

In some embodiments, the therapeutic agent comprises a steroid comprising cyclosporine or a combination of loteprednol etabonate and tobramycin. In some embodiments, the therapeutic agent comprises loteprednol etabonate 0.5% and tobramycin 0.3%. In some embodiments, the therapeutic agent comprises dexamethasone 0.1% and tobramycin 0.3%.

In some embodiments, the composition consists of a therapeutic agent consisting of cyclosporine, and a liquid delivery vehicle consisting of hydroxypropyl methylcellulose (HPMC), mineral oil, and sterile water. In some embodiments, the therapeutic agent comprises of the cyclosporine 0.05%.

In some embodiments, the liquid delivery vehicle comprises about 0.2% w/w of the HPMC, about 20% w/w of the mineral oil, and about 79.8% w/w of the sterile water.

In some embodiments, the spray dispenses about 0.15 ml of the composition to the eye of a patient in a plume or a mist. In some embodiments, the spray dispenses about 0.05 ml to about 50 ml of the composition to the eye in a plume or a mist. In some embodiments, the spray dispenses from about 0.05, 0.06, 0.70, 0.08, 0.09, 0.10, 0.11, 0.12, 0.13, 0.14, 0.15, 0.16, 0.17, 0.18, 0.19, 0.20, 0.25, 0.30, 0.35, 0.40, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5 to about 20 ml of the composition to the eye in a plume or a mist. In some embodiments, the spray facilitates enhanced or better adherence of the composition to the cornea of the eye. In this way, delivery to the affected eye is enhanced.

In some embodiments, the spray dispenses about 50,000 to about 20,000,000 mcg of the composition to the eye in a plume or a mist. In some embodiments, the spray dispenses from about 50,000 to about 200,000 mcg, from about 50,000 to about 100,000 mcg, or from about 50,000 to about 75,000 mcg of the composition to the eye in a plume or a mist.

In some embodiments, the spray dispenses about 0.15 ml of the composition, and about 0.05 ml of the therapeutic agent. In some embodiments, the spray dispenses 0.01, 0.02, 0.03, 0.04, 0.05, 0.06, 0.07, 0.08, 0.09 or 0.10 ml of the therapeutic agent. In some embodiments, the spray dispenses 10,000, 20,000, 30,000, 40,000, 50,000, 60,000, 70,000, 80,000, 90,000, or 100,000 mcg of the therapeutic agent.

In some embodiments, the therapeutic agent, includes, but is not limited to at least one of demulcents; antimycotics, antivirals and other anti-infectives; steroids, NSAIDs, selective cyclooxygenase-2 inhibitors and other anti-inflammatory agents; acetylcholine blocking agents; adrenergic agonists, beta-adrenergic blocking agents and other antiglaucoma agents; antihypertensives; antihistamines; anticataract agents; and topical and regional anesthetics. Illustrative specific drugs include acebutolol, aceclidine, acetylsalicylic acid (aspirin), $N^4$ acetylsulfisoxazole, alclofenac, alprenolol, amfenac, amiloride, aminocaproic acid, ρ-aminoclonidine, aminozolamide, anisindione, apafant, atenolol, bacitracin, benoxaprofen, benoxinate, benzofenac, bepafant, betamethasone, betaxolol, bethanechol, brimonidine, bromfenac, bromhexine, bucloxic acid, bupivacaine, butibufen, carbachol, carprofen, celecoxib, cephalexin, chloramphenicol, chlordiazepoxide, chlorprocaine, chlorpropamide, chlortetracycline, ciclofrofen, cinmetacin, ciprofloxacin, clidanac, clindamycin, clonidine, clonixin, clopirac, cocaine, cromolyn, cyclopentolate, cyproheptadine, demecarium, dexamethasone, dibucaine, diclofenac, diflusinal, dipivefrin, dorzolamide, enoxacin, epinephrine, erythromycin, eserine, estradiol, ethacrynic acid, etidocaine, etodolac, fenbufen, fenclofenac, fenclorac, fenoprofen, fentiazac, flufenamic acid, flufenisal, flunoxaprofen, fluorocinolone, fluorometholone, flurbiprofen and esters thereof, fluticasone propionate, furaprofen, furobufen, furofenac, furosemide, gancyclovir, gentamicin, gramicidin, hexylcaine, homatropine, hydrocortisone, ibufenac, ibuprofen and esters thereof, idoxuridine, indomethacin, indoprofen, interferons, isobutylmethylxanthine, isofluorophate, isoproterenol, isoxepac, ketoprofen, ketorolac, labetolol, lactorolac, latanoprost, levo-bunolol, lidocaine, lonazolac, loteprednol, meclofenamate, medrysone, mefenamic acid, mepivacaine, metaproterenol, methanamine, methylprednisolone, metiazinic, metoprolol, metronidazole, minopafant, miroprofen, MK-663, modipafant, nabumetome, nadolol, namoxyrate, naphazoline, naproxen and esters thereof, neomycin, nepafenac, nitroglycerin, norepinephrine, norfloxacin, nupafant, olfloxacin, olopatadine, oxaprozin, oxepinac, oxyphenbutazone, oxyprenolol, oxytetracycline, parecoxib, penicillins, perfloxacin, phenacetin, phenazopyridine, pheniramine, phenylbutazone, phenylephrine, phenylpropanolamine, phospholine, pilocarpine, pindolol, pirazolac, piroxicam, pirprofen, polymyxin, polymyxin B, prednisolone, prilocaine, probenecid, procaine, proparacaine, protizinic acid, rimexolone, rofecoxib, salbutamol, scopolamine, sotalol, sulfacetamide, sulfanilic acid, sulindac, suprofen, tenoxicam, terbutaline, tetracaine, tetracycline, theophyllamine, timolol, tobramycin, tolmetin, triamcinolone, trimethoprim, trospectomycin, valdecoxib, vancomycin, vidarabine, vitamin A, warfarin, zomepirac, pharmaceutically acceptable salts, and any combination thereof.

In some embodiments, the therapeutic agent comprises a steroid, including, but not limited to at least one of anecortive acetate, tetrahydrocortisol; 4,9(11)-pregnadien-17α,21-diol-3,20-dione, and its -21-acetate salt; 11-epicortisol; 17α-hydroxyprogesterone; tetrahydrocortexolone; cortisona; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its -21-acetate, -21-disodium phosphate, and -21-hemisuccinate forms; triamcinolone benetonide; triamcinolone hexacetonide; fluocinolone and fluocinolone acetate; dexamethasone and its 21-acetate, -21-(3,3-dimethylbutyrate), -21-phosphate disodium salt, -21-diethylaminoacetate, -21-isonicotinate, -21-dipropionate, and -21-palmitate forms; betamethasone and its -21-acetate, -21-adamantoate, -17-benzoate, -17,21-dipropionate, -17-valerate, and -21-phosphate disodium salts; beclomethasone; beclomethasone dipropionate; diflorasone; diflorasone diacetate; mometasone furoate; acetazolamide; loteprednol; difluprednate; fluorometholone, rimexolone, medrysone, fluticasone, budesonide, and cyclosporine. In some embodiments, the therapeutic agent includes anti-neovascularization steroids such as 21-nor-5β-pregnan-3α,17α,20-triol-3-acetate; 21-nor-5α-pregnan-3α,17α,20-triol-3-phosphate; 21-nor-5β-pregn-17(20)en-3α,16-diol; 21-nor-5β-pregnan-3α,17β,20-triol; 20-acetamide-21-nor-5α-pregnan-3α,17α-diol-3-acetate; 313 acetamido-5β-pregnan-11β,17α,21-triol-20-one-21-a-cetate; 21-nor-5α-pregnan-3α,17β,20-triol; 21α-methyl-5β-pregnan-3α,11,17α,21-tetrol-20-1-one-21-methyl ether; 20-azido-21-nor-5β-pregnan-3α,17α-diol; 20(carbethoxymethyl)thio-21-nor-5β-pregnan-3α,17α-diol; 20-(4-fluorophenyl)thio-21-nor-5β-pregnan-3α,17α-diol; 16α-(2-hydroxyethyl)-17β-methyl-5β-androstan-3α,17α-diol; 20-cyano-21-nor-5β-pregnan-3α,17α-diol; 17α-methyl-51-androstan-3α,17β-diol; 21-nor-5β-pregn-17(20)en-3α-ol; 21- or -5β-pregn-17(20)en-3α-ol-3-acetate; 21-nor-5-pregn-17(20)-en-3α-ol-16-acetic acid 3-acetate; 3-azido-5-pregnan-11,17α,21-triol-20-one-21-acetate; and 5β-pregnan-11β,17α,21-triol-20-one; 4-androsten-3-one-17β-carboxylic acid; 17α-ethynyl-5 (10)-estren-17β-ol-3-one; and 17α-ethynyl-1,3,5(10)-estratrien-3,17-diol.

In some embodiments, the therapeutic agent comprises a non-steroidal anti-inflammatory agent (NSAIDs), including, but not limited to at least one of naproxin; diclofenac; celecoxib; sulindac; diflunisal; piroxicam; indomethacin; etodolac; meloxicam; ibuprofen; ketoprofen; r-flurbiprofen; mefenamic; nabumetone; tolmetin, and sodium salts of each of the foregoing; ketorolac bromethamine; ketorolac tromethamine; choline magnesium trisalicylate; rofecoxib; valdecoxib; lumiracoxib; etoricoxib; aspirin; salicylic acid and its sodium salt; salicylate esters of α,β,γ-tocopherols and tocotrienols (and all their d, l, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; and phenylbutazone.

In some embodiments, the therapeutic agent comprises an antibiotic, including but not limited to as least one of gram-negative effective antibiotics such as from aminoglycosides, cephalosporins, diaminopyridines, fluroquinolones, sulfonamides and tetracyclines. Among particular antibiotics of these and other classes, each of the following may illustratively be useful as a gram-negative effective antibiotic: amikacin, azithromycin, cefixime, cefoperazone, cefotaxime, ceftazidime, ceftizoxime, ceftriaxone, chloramphenicol, ciprofloxacin, clindamycin, colistin, domeclocycline, doxycycline, erythromycin, gentamicin, mafenide, methacycline, minocycline, neomycin, norfloxacin, ofloxacin, oxytetracycline, polymyxin B, pyrimethamine, silver sulfadiazine, sulfacetamide, sulfisoxazole, tetracycline, tobramycin and trimethoprim. Gram-negative effective antibiotics are fluroquinolones such as ciprofloxacin, norfloxacin and ofloxacin.

In some embodiments, the therapeutic agent comprises an antiviral, including but not limited, at least one of to iota carrageenan, VIRA-A ophthalmic ointment, (vidarabine). Opthalmic quinalones include, for example, CHIBROXIN (norfloxacin ophthalmic solution); CILOXAN ophthalmic solution, (Ciprofloxacin HCL); and Ocuflox ophthalmic solution (ofloxacin). Opthalmic sulfonamides include, for example, BLEPHAMIDE ophthalmic ointment (sulfacetamide sodium and prednisolone acetate); and BLEPHAMIDE ophthalmic suspension (sulfacetamide sodium and prednisolone acetate).

In some embodiments, the therapeutic agent comprises an antifungal, including, but not limited to, at least one of natamycin, amorolfine, amphotericin B, anidulafungin, butoconazole, butenafine, caspofungin, ciclopirox olamine, clotrimazole, econazole, fluconazole, flucytosine, griseoulvin, haloprogin, itraconazole, ketoconazole, micafungin, miconazole (including miconazole nitrate), naftifine, nikkomycin Z, nystatin (topical and liposomal), oxiconazole, posaconazole, pimaricin, ravuconazole, sulconazole, terbinafine, terconazole, tioconazole, tolnaftate, undecylenate, voriconazole, or a salt thereof.

In some embodiments, the therapeutic agent comprises mast cell stabilizers, including, but not limited to, at least one of olopatadine, derivatives of olopatadine, alcaftidine, derivatives of alcaftadine, spleen tyrosine kinase inhibitors, and dihydropyridines.

In some embodiments, the therapeutic agent comprises cytokine inhibitors, including, but not limited, at least one of to mitogen-activated kinases (MAP kinase, p38 kinase), c-jun N-terminal kinase (JNK) and 1-kappa kinase (IKK). Also, inhibitors of enzymes which convert precursors of the pro-inflammatory cytokines IL-1β (ICE, IL-1 converting enzyme) and TNFα (TACE, TNF-alpha converting enzyme) to the active species or inhibit the translation of cytokine mRNA provide dry eye therapy. Cytokines promote further synthesis of pro-inflammatory cytokines through activation of Janus family tyrosine kinase (JAK) and signal transducers and activators of transcription (STAT) and, therefore, inhibitors of JAKs and STATs provide treatment of dry eye. Inhibitors of activator protein-1 (AP-1) suppress cytokine synthesis in ocular surface cells and provide dry eye therapy. Additionally, ligands of retinoid X receptors (RXR) are known to suppress cytokine synthesis in epithelial cells and are suitable for use in the present invention. Inhibitors of MAP kinases (p38) include (5-(2-amino-4-pyrimidinyl)-4-(4-fluorophenyl)-1-(4-piperidinyl)imidazole) ["SB-220025"]. Inhibitors of JNK include anthra[1,9-cd]pyrazol-6(2H)-one ["SP-600125"]. Inhibitors of ICE include pralnacasan (HMR3480/VX-740). TNF mRNA translation inhibitors include (D)Arginyl-(D)Norleucyl-(D)Norleucyl-(D)Arginyl-(D)Norleucyl-(D)Norleucyl-(D)Norleucyl-Glycine-(D)Tyrosine-amide,acetate salt ["RDP58"]. NFkB inhibitors include 2-chloro-N-[3,5-di(trifluoromethyl)phenyl]-4-(trifluoromethyl)pyrimidine-5-carboxamide ["SP-100030"], and triflusal. AP-1 inhibitors include SP-100030. RXR agonists include bexarotene. In some embodiments, the cytokine inhibitor is lifitegrast.

In some embodiments, the composition comprises ophthalmically acceptable acids, which act as interactive agents to retard release of the drug/therapeutic agent. Acids useful as interactive agents include boric, lactic, orthophosphoric, citric, oxalic, succinic, tartaric and formic glycerophosphoric acids.

In some embodiments, the composition comprises a solubilizer that is added to the composition to provide solubility of the selected therapeutic agent. Solubilizers that may be used include, but are not limited to polyoxyethylene glycol ethers, polyethylene glycol higher fatty acid esters, and polyoxyethylene fatty acid esters.

In some embodiments, the composition comprises a surfactant. In some embodiments, the surfactant acts as detergents, wetting agents, emulsifiers, foaming agents, and/or dispersants. In some embodiments, the composition comprises an ophthalmologically acceptable surfactant to assist in dissolving the drug/therapeutic agent. In some embodiments, the composition comprises a thickener such as hydroxymethylcellulose, hydroxyethylcellulose, hydroxypropylmethylcellulose, and/or methylcellulose, polyvinylpyrrolidone. In some embodiments, the surfactant includes, but is not limited to oleoyl macrogolglycerides (for example, Labrafil™ M 1944CS (Gattefosse, France), etc.), linoleoyl macrogolglycerides (for example, Labrafil™ M 2125CS (Gattefosse, France), etc.), caprylocaproyl polyoxylglycerides (for example, Labrasol™ (Gattefosse, France), etc.), polyoxyl 35 hydrogenated castor oil (for example, Cremophor™ EL (BASF, Germany), Cremophor™ ELP (BASF, Germany), etc.), polyoxyl 40 hydrogenated castor oil (for example, Cremophor™ RH40 (BASF, Germany), etc.), a condensation product of ethylene oxide with 12-hydroxystearic acid (for example, Solutol™ HP15 (BASF, Germany), etc.), and polysorbate 80 (Croda, England). In some embodiments, the surfactant may be present in an amount ranging from about 0.01 to 6% w/w, w/v or v/v based on the total weight of the composition. In some embodiments, the surfactant is present in an amount of from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, or 6% w/w, w/v or v/v based on the total amount of the composition.

Method of Treating an Ophthalmic Condition

A method of treating an ophthalmic condition is provided. In some embodiments, the ophthalmic condition is dry eye, known as keratoconjunctivitis sicca. In some embodiments, the condition includes, but is not limited to meibomitis, conjunctivitis, iritis, age-related macular degeneration, glaucoma, a corneal laceration, exposure keratopathy, corneal ulcer, corneal scar and/or a traumatic corneal abrasion. In some embodiments, the patient includes, but is not limited to an animal, such as a human, dog, cat, horse, hamster, pig, cow, bird, bunny, chicken, goat, and/or a sheep. In some embodiments, the patient is an elderly human, a child or a person suffering from an illness.

In some embodiments, the method comprises administering an effective amount of the ophthalmic composition in a spray comprising a lubricant comprising hydroxypropyl methylcellulose (HPMC), mineral oil, and sterile water to an eye of the patient. In some embodiments, the composition further comprises a therapeutic agent and the lubricant is a delivery vehicle for the therapeutic agent. In some embodiments, the spray facilitates enhanced or better adherence of the composition to the cornea of the eye.

In some embodiments, the composition is administered via a spray that is dispensed from an aerosol bottle or a non-aerosol bottle. Before administration to the eye, the bottle is vigorously shaken for a period of time to form an emulsion. The spray then administers the composition to the eye via a spray plume or mist. In some embodiments, the spray plume or mist can deliver a varying or specific amount of the composition to the eye of the patient. In some embodiments, the spray plume or mist can be manipulated into various sizes, shapes, lengths, various disbursing angles, degrees of intensity, duration and velocities depending on the type of bottle used to deliver the composition to the eye.

In some embodiments, the spray administers a fine mist of liquid droplets. In some embodiments, the average size of the droplets is from 2 to about 180 microns in diameter. In some embodiments, the average size of the fluid droplets from about 2 to about 100 microns, from about 20 to about 100 microns, from about 40 to about 100 microns, from about 60 to about 100 microns. In some embodiments, the droplets have a diameter between 5 and 80 microns, from about 10 and 70 microns, from about 20 and 50 microns, from about 30 and 40 microns in diameter. In some embodiments, the droplets have a diameter from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 microns in diameter.

In some embodiments, the spray administers a mist that can be a cloud of droplets from 10-60 microns, having a freefall time (existence time per minute) of about less than 1 to about 6 seconds and a terminal velocity 15-110 mm/sec. In some embodiments, the visual appearance of such a mist is separate droplets. In some embodiments, a less-fine mist is administered having a cloud of droplets of 5β-150 microns, characterized by a freefall time (existence time per minute) of about 0.1 to about 0.3 seconds and a terminal velocity 5β-600 mm/sec. In some embodiments, the visual appearance of the mist is separate droplets.

In some embodiments, the spray is administered at a particular momentum. In some embodiments, the momentum (kg·m/sec) of the cloud is about $1\times10^4$ or $1\times10^5$ for a less fine mist, or $10^5$-$1\times10^{-6}$ for a mist.

In some embodiments, the ophthalmic composition comprises about 0.1% w/w to about 5% w/w of the HPMC, about 2% w/w to about 33% w/w of the mineral oil, and about 62% w/w to about 97% w/w of the sterile water. In some embodiments, the composition further comprises a therapeutic agent and the lubricant acts as a delivery vehicle for the therapeutic agent. The composition comprises one part therapeutic agent to two parts drug delivery vehicle.

In some embodiments, the spray administers 0.15 ml of the ophthalmic composition to the eye in a single dose. Out of the 0.15 ml of the composition, 0.05 ml is the therapeutic agent. In some embodiments, about 0.05 to about 0.30 ml of the composition is administered to the eye. In some embodiments, about 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29 to about 0.30 ml of the composition is administered to the eye. In some embodiments, multiple doses of the composition is administered to the eye. In some embodiments, 1 to about 6 doses of the composition is administered to the eye every 24 hours. In some embodiments, 1, 2, 3, 4, 5 or 6 doses of the composition is administered to the eye every 24 hours. In some embodiments, 1, 2, 3, 4, 5 or 6 doses of the composition is administered to the eye every 6, 12, 18, 24, 30, 36, 42 or 48 hours.

In some embodiments, the composition is administered to the patient for a period of 1, 2, 3, 4, 5, 6, 7, 8, 9, 10, 11, 12, 13 or 14 weeks. In some embodiments, the composition is administered to the patient indefinitely.

In some embodiments, the composition is administered via a spray that is dispensed from a non-aerosol bottle that comprises a built-in purifying filter. The built-in purifying filter facilitates a preservative free composition. In some embodiments, the filter is in the tip of the bottle to prevent bacteria from entering the bottle, allowing the composition to be preservative free. In some embodiments, the filter is gas-permeable, allowing air into the bottle only to ensure one-way flow of the composition during administration.

Having now generally described the invention, the same may be more readily understood through the following reference to the following examples, which are provided by way of illustration and are not intended to limit the present invention unless specified.

EXAMPLES

Example 1

The ophthalmic composition was prepared as follows: 1 ml of hypromellose 2.5% (commercially available) was diluted in 9 ml of sterile water to yield a solution of hypromellose 0.25%. The 10 ml solution was then mixed with 2.5 ml of mineral oil (commercially available), yielding a final concentration of hypromellose 0.2% and mineral oil 20%, as shown in Table 1 below. The 12.5 ml emulsion was then shaken vigorously and placed in a non-aerosol spray bottle. Each spray yielded 0.15 ml of the ophthalmic composition, delivering a total of 100 sprays for each 15 ml of solution.

TABLE 1

| Ophthalmic composition | | | |
|---|---|---|---|
| Hypromellose solution: 10 ml | 1 ml of Hypromellose 2.5% | 9 ml of sterile water | Final yield: Hypromellose 0.25% |
| Ophthalmic composition: 12.5 ml | 10 ml Hypromellose solution | 2.5 ml of mineral oil | Final yield: Hypromellose 0.2% |

Example 2

A therapeutic agent comprising a loteprednol etabonate 0.5% and tobramycin 0.3% ophthalmic suspension was mixed with the ophthalmic composition prepared in Example 1. This mixture comprised two parts ophthalmic composition to one-part therapeutic agent. The resulting composition was then administered to a subject (a Shih Tzu dog), as shown in FIG. 1 diagnosed with dry eye who suffered from redness, inflammation, crust and a corneal scar. The composition was administered twice a day for three weeks to the subject. The subject showed physical improvements, as shown in FIG. 2 such as a loss of the redness, no inflammation and no crust formation. The corneal scar was still present but started to fade. After treatment discontinued, inflammation of the eye returned.

Example 3

After discontinuation of treatment occurred in Example 2, a therapeutic agent comprising a cyclosporine ophthalmic emulsion at 0.05% was mixed with the ophthalmic composition prepared in Example 1. This mixture comprised two parts ophthalmic composition to one-part therapeutic agent. The resulting composition was then administered to subject from Example 2 that now suffered with inflammation. The composition was administered twice a day for four weeks. The subject showed physical improvements such as a decrease in inflammation.

Example 4

It is contemplated that a loteprednol etabonate 0.5% and tobramycin 0.3% ophthalmic suspension can be added to a spray bottle and then administered to an eye of a patient. The suspension can be administered twice a day for about 4 weeks. The suspension would have a low viscosity and would not cause any significant visual blur but would be less adherent to a cornea.

Example 5

It is contemplated that a therapeutic agent comprising a cytokine inhibitor comprising lifitegrast at a selected amount is added to the composition of Example 1. This composition can then be added to a spray bottle and administered to the eye of a patient. It is also contemplated that only the cytokine inhibitor comprising lifitegrast at a selected amount is added to a spray bottle for administration to the eye of a patient.

Example 6

Four plastic eye models, as shown in FIGS. 3 to 6 were used to simulate the conditions of a mammalian eye in order to determine the percentage of mineral oil in the ophthalmic spray composition that would improve adherence to the cornea of an eye. Corneal adherence is important because the ophthalmic composition will cause a greater therapeutic effect the longer that it is adhered to the cornea. This is particularly important in a spray formulation since run-off will reduce the therapeutic effect as the composition will not adhere to the cornea to obtain an enhanced therapeutic benefit.

Figure 3:
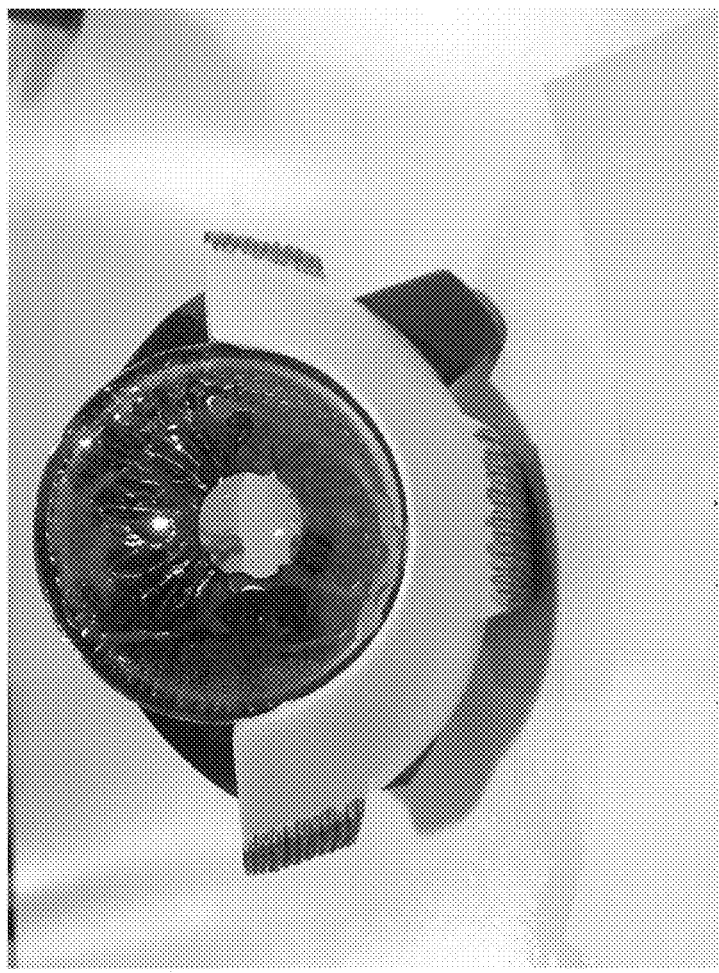
FIG. 3 is a picture of a plastic eye model that has been sprayed with a composition comprising undiluted 0.05% cyclosporine to demonstrate how the composition adheres to the cornea of the eye.
Figure 4:
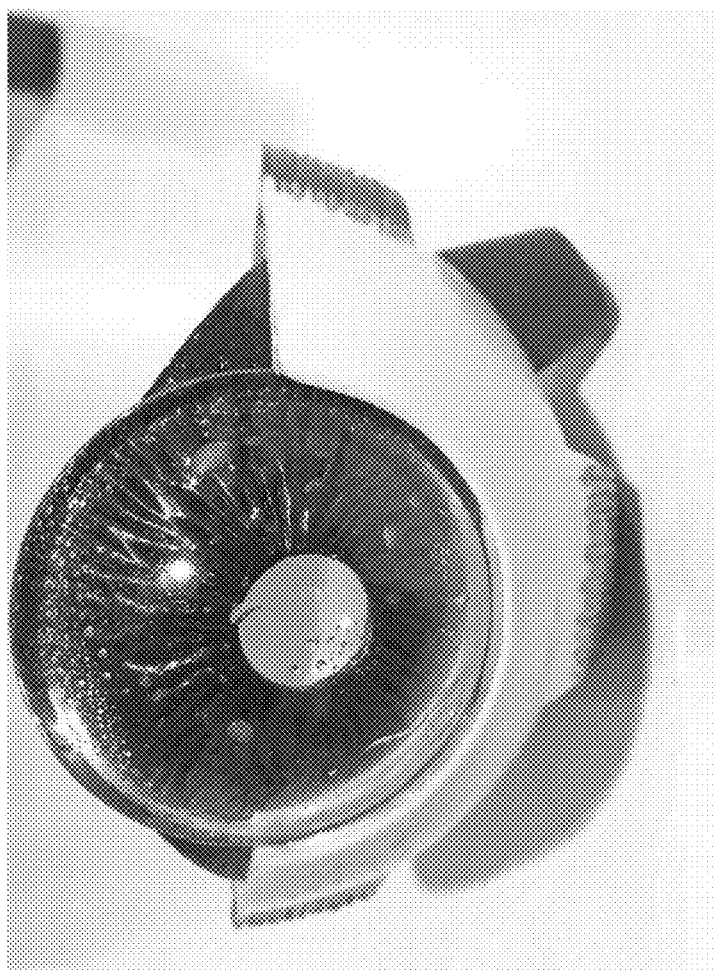
FIG. 4 is a picture of a plastic eye model that has been sprayed with a composition comprising 0.2% HPMC, 5% mineral oil, and 94.8% sterile water to demonstrate how the composition adheres to the cornea of the eye.
Figure 5:
FIG. 5 is a picture of a plastic eye model that has been sprayed with a composition comprising 0.2% HPMC, 20% mineral oil, and 79.8% sterile water to demonstrate how the composition adheres to the cornea of the eye.
Figure 6:
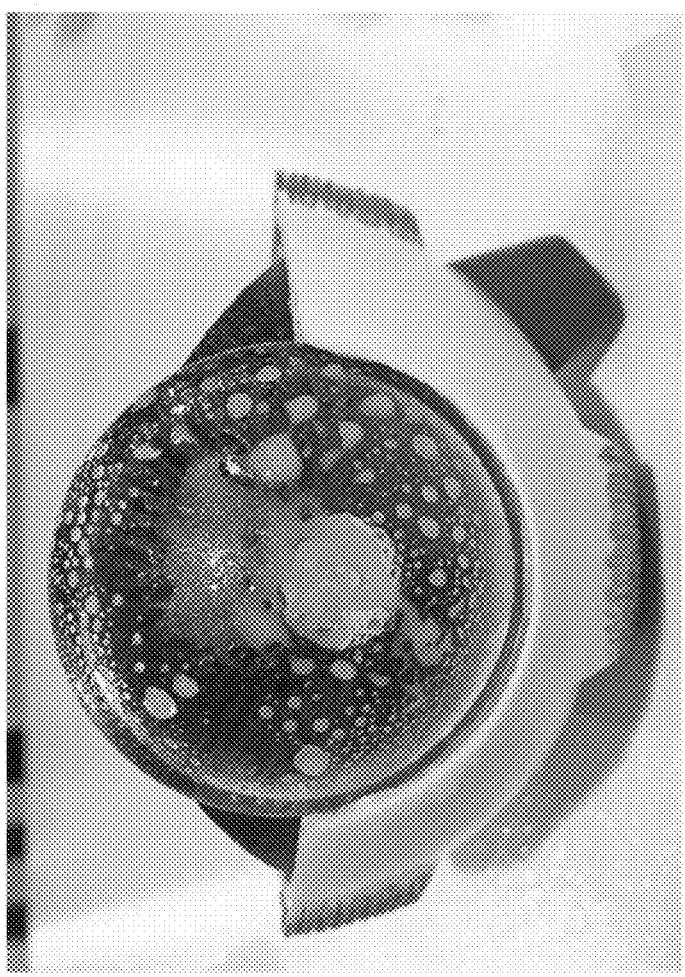
FIG. 6 is a picture of a plastic eye model that has been sprayed with a composition comprising 0.2% HPMC, 33.3% mineral oil, and 66.5% sterile water to demonstrate how the composition adheres to the cornea of the eye.

The first eye model was sprayed with a composition comprising undiluted 0.05% cyclosporine, as shown in FIG. 3. The second eye model was sprayed with a composition comprising 0.2% HPMC, 5% mineral oil, and 94.8% sterile water, as shown in FIG. 4. The third eye model was sprayed with a composition comprising 0.2% HPMC, 20% mineral oil, and 79.8% sterile water, as shown in FIG. 5. Finally, the fourth eye model was sprayed with a composition comprising 0.2% HPMC, 33.3% mineral oil, and 66.5% sterile water.

Results showed that the first eye model sprayed with a composition comprising undiluted 0.05% cyclosporine dripped off the eye (i.e., run-off) and did not adhere well to surface of the eye. The second eye model sprayed with a composition comprising 0.2% HPMC, 5% mineral oil, and 94.8% sterile water adhered to the eye better than the composition administered in the first eye model. The third eye model sprayed with a composition comprising 0.2% HPMC, 20% mineral oil, and 79.8% sterile water, also adhered to the eye better than the first eye model. The fourth eye model sprayed with a composition comprising 0.2% HPMC, 33.3% mineral oil, and 66.5% sterile water adhered to the eye better than the second and third eye models, and also created a "clumping effect" on the surface of the eye. These results show that by using HPMC and increasing the concentration of mineral oil in sterile water, a spray can be achieved that can deliver a therapeutic agent or wet the affected eye better than a commercially available off the shelf eye composition.

Having described various embodiments of the application with reference to the accompanying drawings, it is to be understood that the application is not limited to those precise embodiments, and that various changes and modifications may be effected therein by one skilled in the art without departing from the scope or spirit of the application as defined in the appended claims. Such modifications include substitution of components for components specifically identified herein, wherein the substitute components provide functional results which permit the overall functional operation of the present application to be maintained. Such substitutions are intended to encompass presently known components and components yet to be developed which are accepted as replacements for components identified herein and which produce result compatible with operation of the present application.

What is claimed is:

1. An ophthalmic composition for administration in a spray to the eye, the ophthalmic composition consisting of: a therapeutic agent; and a liquid delivery vehicle, the liquid delivery vehicle consisting of hydroxypropyl methylcellulose (HPMC) in an amount of about 0.2% w/w, mineral oil in an amount of about 20% w/w, and sterile water in an amount of about 79.8% w/w.

2. An ophthalmic composition according to claim 1, wherein the ophthalmic composition is one-part therapeutic agent to two parts liquid delivery vehicle.

3. An ophthalmic composition according to claim 1, wherein the therapeutic agent is selected from the group consisting of a steroid, an antimicrobial, a cytokine inhibitor, an antihistamine, NSAIDS, leukotriene inhibitors or a combination thereof.

4. An ophthalmic composition according to claim 1, wherein the therapeutic agent is selected from the group consisting of a steroid comprising cyclosporine or a combination of loteprednol etabonate or dexamethasone and tobramycin.

5. An ophthalmic composition according to claim 1, wherein the therapeutic agent consists of cyclosporine.

6. An ophthalmic composition according to claim 1, wherein the therapeutic agent is loteprednol etabonate at 0.5% w/w and tobramycin at 0.3% w/w.

7. An ophthalmic composition according to claim 1, wherein the therapeutic agent is cyclosporine at 0.05% w/w.

8. A method of treating an ophthalmic condition in a patient suffering therefrom, the method comprising: administering an effective amount of an ophthalmic composition in a spray consisting of a lubricant consisting of hydroxypropyl methylcellulose (HPMC) in an amount of about 0.2% w/w, mineral oil in an amount of about 20% w/w, and sterile water in an amount of about 79.8% w/w to an eye of the patient, and the ophthalmic condition is keratoconjunctivitis sicca.

9. A method according to claim 8, wherein the spray is dispensed in an aerosol bottle or a non-aerosol bottle that administers the ophthalmic composition to the eye via a spray plume.

10. A method according to claim 8, wherein 0.15 ml of the ophthalmic composition is administered to the eye.

* * * * *